United States Patent [19]

Babington

[11] E Re. 30,285

[45] Reissued May 27, 1980

[54] SPRAYING DEVICES, IN PARTICULAR NEBULIZING DEVICES

[76] Inventor: Robert S. Babington, 1113 Ingleside Ave., McLean, Va. 22101

[21] Appl. No.: 765,724

[22] Filed: Feb. 4, 1977

Related U.S. Patent Documents

Reissue of:

[64] Patent No.: 3,864,326
Issued: Feb. 4, 1975
Appl. No.: 255,681
Filed: May 22, 1972

[51] Int. Cl.[2] ..... F02M 15/04

[52] U.S. Cl. ..... 261/78 A; 239/337; 239/338; 239/418; 261/DIG. 65; 261/142

[58] Field of Search ..... 239/3, 220, 338, 339, 239/337, 418, 426; 261/78 A, DIG. 65, 36 R, 115, 116, 142

[56] References Cited

U.S. PATENT DOCUMENTS

| | | | |
|---|---|---|---|
| 1,568,840 | 1/1926 | Holmes | 239/338 |
| 1,859,935 | 5/1932 | Potts et al. | 239/418 |
| 2,582,805 | 1/1952 | Trumbour et al. | 239/338 |
| 2,869,188 | 1/1959 | Cameto | 239/338 X |
| 3,018,971 | 1/1962 | Cheney | 239/338 |
| 3,406,913 | 10/1968 | Frangos | 239/337 X |
| 3,421,699 | 1/1969 | Babington et al. | 261/78 A X |
| 3,425,059 | 1/1969 | Babington | 261/78 A X |
| 3,584,192 | 6/1971 | Maag | 261/141 X |

*Primary Examiner*—Othell M. Simpson
*Assistant Examiner*—W. D. Bray
*Attorney, Agent, or Firm*—Pollock, Vande Sande & Priddy

[57] ABSTRACT

A relatively simple air or air-oxygen powered device utilizing the principles disclosed in U.S. Pat. Nos. 3,421,692 and 3,421,699 comprises means for feeding liquid to the atomizing sphere and the combination of multiple spray producing sources and treatment of atomized particles by various techniques to produce extremely dense mists or fogs adapted for inhalation by human subjects.

26 Claims, 11 Drawing Figures

Figure 1:
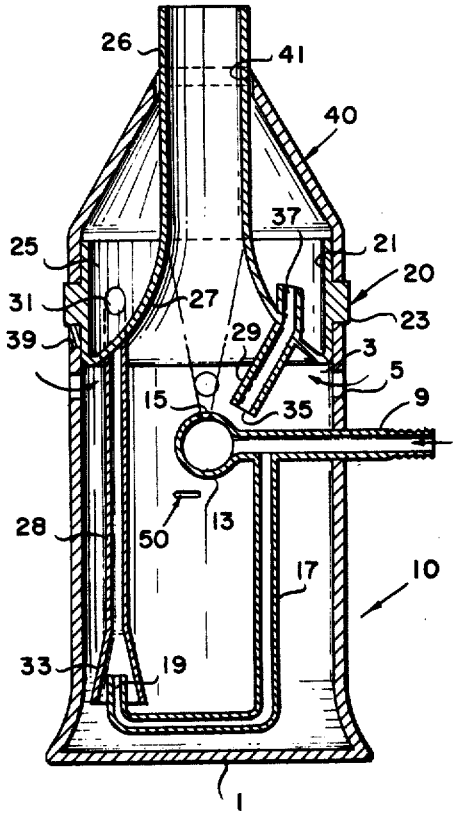

Fig. 3
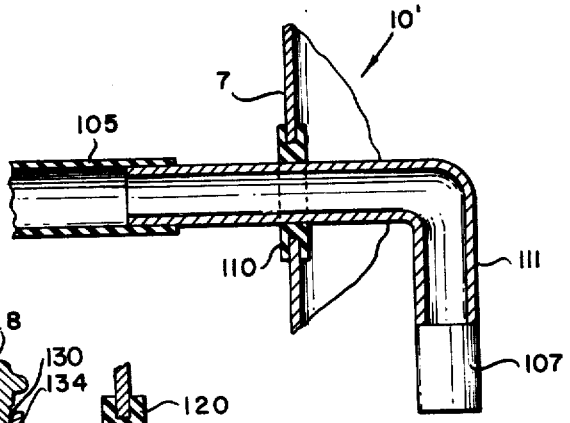
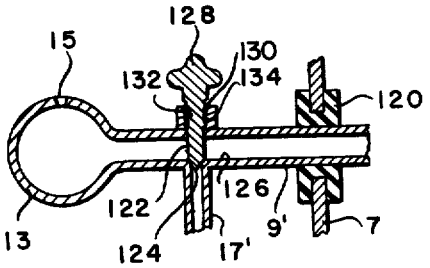
Fig. 4
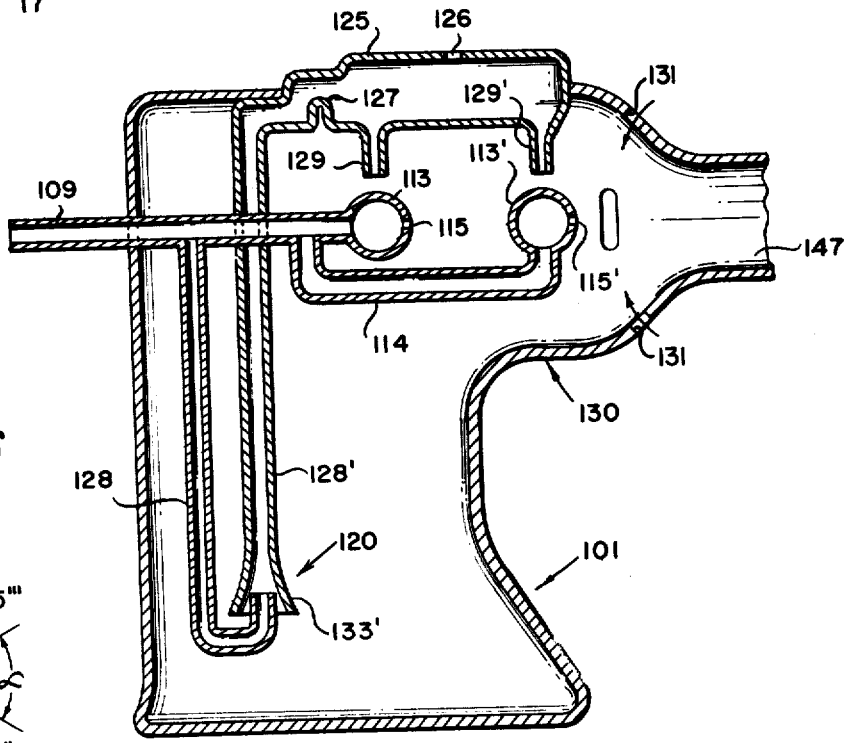
Fig. 6
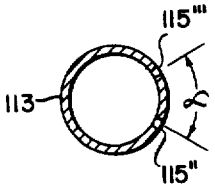
Fig. 6a

Fig. 7
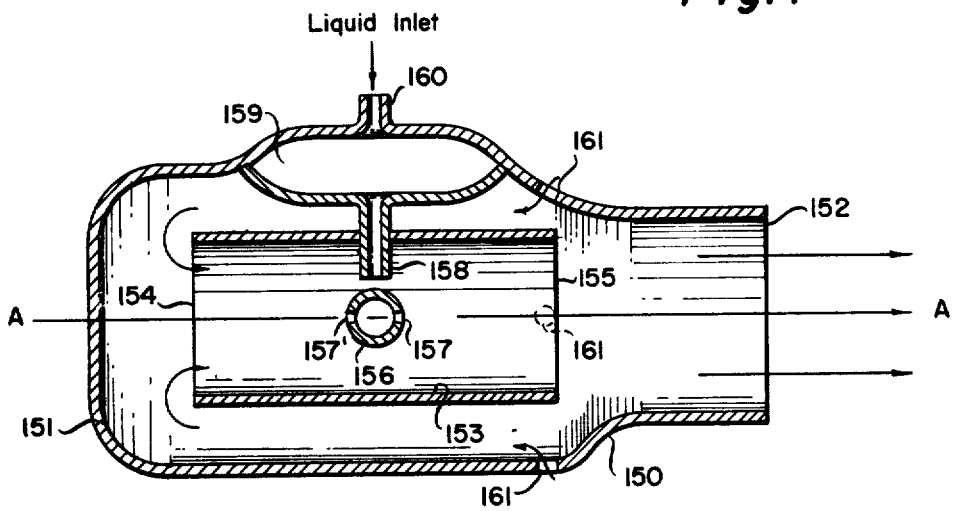
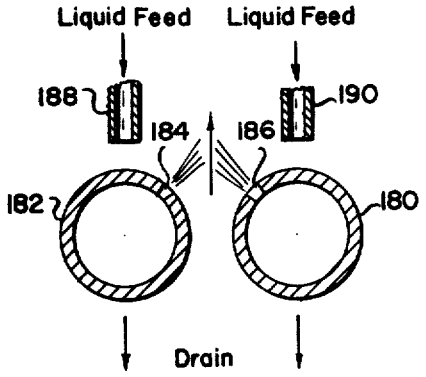
Fig. 8
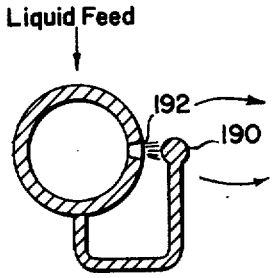
Fig. 9
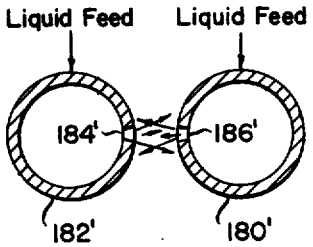
Fig. 10

SPRAYING DEVICES, IN PARTICULAR NEBULIZING DEVICES

Matter enclosed in heavy brackets [ ] appears in the original patent but forms no part of this reissue specification; matter printed in italics indicates the additions made by reissue.

BACKGROUND MATERIAL

In the treatment of many respiratory ailments it is desirable to treat the patient by means of aerosolized water or medicants which are inhaled directly into the lungs. In some cases the sought-for benefit can be obtained by enveloping the patient or, at least the trunk, head and shoulders of the patient in a sealed housing into which the medicant is introduced in aerosolized form, along with the necessary breathing air. Specific examples of such arrangements are croup tents, oxygen tents, incubators and the like. In other cases, it is essential that the medicants be introduced directly into the human or animal respiratory tract by connection of the patient to the nebulizer via surgical incision. An example of such circumstances is the treatment of patients recovering from extensive throat surgery in which a tracheotomy is required. In other cases, it suffices that a patient be treated by simply humidifying the atmosphere surrounding him or her as in many times accomplished in the home by room vaporizers and the like.

Regardless of how used or by what name identified, a successful medical nebulizer, vaporizer or atomizer should a. be able to introduce a liquid preparation which may be water or some type of medicant into the carrier fluid to effect sufficient application of the medicant, b. be able to vaporize or atomize the medicant into an aerosol form which is comprised of a maximum of small high-respirable particles, c. be simple in operation, easily cleanned and sterilized and low in cost and maintenance.

As a result of these requirements and having in mind that, while an ideal nebulizer should meet each to the ultimate degree of refinement, the practical fact is that a home vaporizer need not be as refined as the equipment used in a hospital. Similarly, a nebulizer source to a crop tent would deliver a higher capacity of aerosol than a device used for post-operative treatment by direct respiratory tract application. Obviously, too, the cost of a home vaporizer differs radically from the cost of more sophisticated hospital equipment because hospital equipment should meet all of the stated requirements to the ultimate degree.

In view of such wide variations in application and requirements, there are on the market a wide variety of medical nebulizers of atomizers varying from the so-called steam vaporizers, available at any drug store, at a price of less than Twenty Dollars to the much more sophisticated and complex ultrasonic nebulizers sold to hospitals or individuals through medical supply houses and costing over Five Hundred Dollars. To date, there is not available one single piece of nebulizing equipment which can be sold at a reasonable price yet which will meet the wide variety of applications from simple home use to carefully regulated hospital techniques.

In recent times, a new technique has evolved for producing very fine spray of liquids. This technique involves the provision of dynamic film of liquid on a suitable surface and traversing the film with a stream of comparatively low pressure air whereby a portion of the film is atomized and carried from the surface in spray form. The fundamental concept is described and claimed in the U.S. Pat. Nos. 3,421,699 and 3,421,692, both dated Jan. 14, 1969 and issued to Robert S. Babington et al.

Preliminary studies of the technique proved the feasibility of producing a nebulizer capable of aerosolizing liquids to such a fine degree and in such dense form as to enable same to be inhaled directly into the respiratory tracts of human subjects. These studies further indicated that such a nebulizer was not only feasible but highly desirable because it would be simple in operation, relatively inexpensive, easy to maintain and above all, that by the application of various techniques and modifications of the basic apparatus such devices could be produced to meet the need for practically any type of inhalation therapy from simple croup tents to direct introduction of the aerosolized liquids into the respiratory tract.

The present invention deals with nebulizing devices and techniques to accomplish the desired results.

Accordingly, an object of the present invention is to provide a simple, easily used, inexpensive nebulizer capable of general medical use.

Another object of the invention is to produce a nebulizer which is capable of atomizing medicants to the ultimate degree of fineness to permit direct introduction of the medicant into the respiratory system of a patient.

An additional object of the invention is to produce a nebulizer which is virtually foolproof in operation and application.

Still another object of the invention is to produce a nebulizer which can be easily and simply cleaned.

A further object of the invention is to produce a nebulizer which is completely reliable and devoid of complex, expensive electronic or mechanical parts.

Still a further object of the invention is to produce a nebulizer which is so inexpensive as to permit the average patient to be able to afford proper respiratory therapy at home.

A further object of the invention is to produce a nebulizer which provides a maximum number of highly-respirable particles per volume of carrier air, so that with each breath a patient derives maximum benefit from the therapeutic aerosol.

These and an obvious myriad of other objects of the invention, not specifically set forth, but apparent to those skilled in the art, may be accomplished by utilizing the principles of atomizing liquids set forth in Babington et al. U.S. Pat. Nos. 3,421,692 and 3,421,699 in the form of a neublizer comprised of a base receptacle or flask; a spherical plenum having at least one aperture therein; air pressure means communicating with said plenum; feed means for depositing water or medicant in liquid form over said spherical plenum, said means may include an air lift pump for lifting liquid from the bottom of the base flask; a holding reservoir receiving the output of said pump, said holding reservoir having outlet means adjacent said plenum for depositing said medicant on said plenum surface. Heater means may be provided in the bottom of said chamber and means may be provided for automatically replenishing the medicant to the base receptacle. Additionally, the nebulizer may include spray impactor means for further reducing particle sizes of the aerosolized medicants or liquids and combinations of plenums and impactors may be provided to increase mass median density and capacity of a nebulizer to meet varying conditions and requirements.

Figure 2:
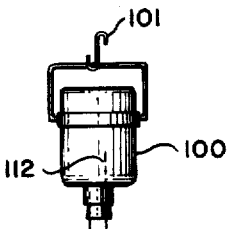
Figure 2:
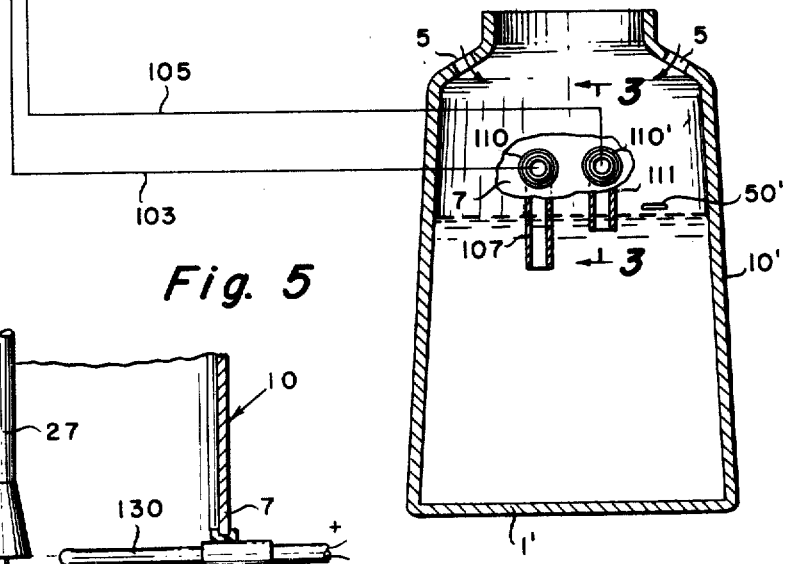
Figure 5:
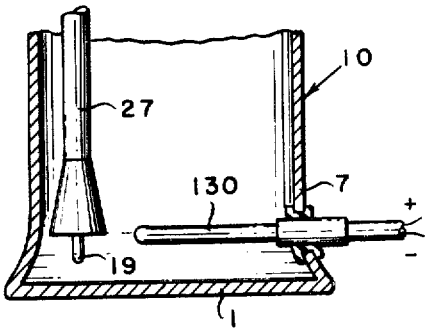

Having broadly defined the inventive concepts herein involved, a further comprehension thereof may be gained from a consideration of the following detailed description, wherein reference will be made to the drawings comprising an integral part of such descriptive matter and wherein:

FIG. 1 is a side sectional elevational view of a basic medical nebulizer,

FIG. 2 is a sectional view of a modified form of the structure of the main chamber shown in FIG. 1, FIG. 3 is a partial sectional view of the syphon/-vacuum actuated filling tubes shown in FIG. 2, FIG. 4 is a sectional view of a modified form of plenum chamber, FIG. 5 is a sectional view of a further modification of the basic invention, FIG. 6 is a side elevational view of a high density vapor producing modification utilizing the basic principles of the invention, FIG. 6a is a partial sectional view showing a plenum sphere modified to include two air discharge ports or slots and particularly adapted for use in the FIG. 6 configuration, FIG. 7 is a partial sectional view showing a further modification of the invention, FIG. 8 is a schematic view showing an alternative position for dual aerosol-Creating sources, FIG. 9 is a schematic view showing modification of the apparatus by the use of an impactor, which modification is particularly applicable to the basic concepts as shown in FIGS. 1, 6 and 7, and FIG. 10 is a further modification of the fundamental concept of the nebulizer and may be used in any of the disclosed configurations, as for example FIGS. 1, 6 and 7.

Considering now FIG. 1, it should be understood that the disclosure is that of the most simple, easily fabricated form of the invention, as well as the materials from which it may be fabricated. Various additions may be made thereto and any one of any number of materials, alone or in combination, may be used to fabricate the structure. The essential requirement for the material or materials selected is that they be non-porous and non-corrosive or non-rusting or have a surface that is non-absorptive; can withstand relatively high temperatures, so the apparatus may be autoclaved for sterilization; and are relatively durable so as to minimize breakage and the like.

Turning now to FIG. 1, a basic and simple form of a nebulizer incorporating the inventive concepts is disclosed. The main part of the nebulizer comprises an open-topped base receptacle or flask 10 in this case made of glass which may be tempered to prevent breakage. Preferably the bottom 1 of the base receptacle 10 is somewhat wider than an open top 3 so as to provide for additional stability to prevent spilling or tipover of the base flask.

As is also shown in FIG. 1, the base flask 10 is provided with a series of openings 5 in its cylindrical side wall 7; these openings being spaced below the open top 3 at a given distance as will be apparent subsequently.

Extending through side wall 7 is a tube 9 which terminates at one end within the base flask 10 in a bulbous or spherical plenum chamber 13 having a small aperture 15 in its uppermost surface. The opposite end of tube 9 extends outwardly of wall 7 a sufficient distance to enable friction engagement thereon of a flexible tube (not shown) which in turns is connected to a suitable source of air or oxygen under pressure.

The tube 9 is also provided with a small bore, branch conduit 17 which, as shown, extends downwardly toward the bottom of flask 10 and runs across the lowermost portion thereof closely adjacent the bottom 1 to terminate in an upwardly extending leg 19. This tubular conduit 17 defines an air pump tube.

The assembly of tube 9, chamber 13 and branch conduit 17, etc., is shown as fabricated of glass because this material is easy to form and, as taught in the aforesaid Babington et al. patents, the glass plenum chamber provides a surface upon which it is easy to obtain the filming of liquid medicant (for which the carrier is usually water, or in sone cases just plain water, in order to obtain the proper spray or aerosol fineness and density.

Seated on top of base flask 10 is a closure assembly 20. Again, while many materials are suitable, the closure assembly is illustrated as being formed from glass. As shown it comprises a cylindrical collar 21 having an annular lug 23 on the outside. Lug 23 defines a support which rests on the rim of top 3 of base flask 10. The bottom of the collar 21 merges with the divergent, generally conical lower end 27 of an exhaust chimney 26. Thus, the collar 21 and the chimney wall 27 define an annular receptacle which forms, as will become apparent, a holding or water/air separating reservoir 25 for the liquid which is to be ultimately nebulized.

Depending from reservoir 25 are two tubular conduits 28 and 29. As clearly shown in FIG. 1, tube 28 opens at 31 to the interior of chamber 25 and extends downwardly to a terminus 33 disposed adjacent the bottom 1 of base flask 10 and defines a lift tube or bubble pump for lifting liquid from base flask 10 to holding reservoir 25.

Tubular member 29 also extends downwardly and has a lower end 35 disposed only slightly below the bottom of holding reservoir 25 and its upper end 37 disposed within holding reservoir 25; preferably, but not necessarily the end 37 is spaced slightly above the lowermost point thereof. Tubular member 29 defines a nebulizer feed tube.

The closure assembly 20 as described, is so seated on the top of base reservoir 10 that the lower end 33 of tube 28 is telescoped over the upper leg 19 of air feed branch line 17. Also the tube 29 is arranged so that it has its lower discharge end 35 disposed adjacent plenum chamber 13 to one side (approximately the two o'clock position), of the aperture 15 where, as shown, the aperture 15 is located at the twelve o'clock position through the plenum wall. The necessity for the proper positioning of cover assembly 20 in base receptacle 10 will become obvious when the operation of the apparatus is described. It suffices to say here that proper registration between the parts can be assured by the provision of a suitable registration tongue 39 at any appropriate place on collar 21, a purely conventional arrangement to assure registration of assembled parts.

The final element of the assembled nebulizer or atomizer is a dome-shaped cap 40 which rests on the top of the annular lung 23 on collar 21 of closure assembly 20 and forms, with holding receptacle 25, a vented chamber. The upper end of the lid 40 is provided with a central opening 41 which is somewhat larger than chimney end 26 so that when assembled, an annular space for venting is provided between chimney 26 and opening 40, when the lid is positioned with its bottom abutting the top of the annular lug 23.

OPERATION OF BASIC NEBULIZER

The operation of the nebulizer, as described, is uncomplicated and requires no particular skill. Before closure assembly 20 and lid 40 are placed on base receptacle 10, this receptacle is filled to about two thirds with the liquid to be nebulized or vaporized. A suitable mark, such as a fill line 50 may be provided as indicator on the wall of base flask 10. After closure assembly 20 and lid 40 are placed on base receptacle 10, a suitable source of gas under pressure is supplied to the serrated end of tube 9 by means of a flexible tubing in communication with a source of compressed air or gas. This compressed air source may be a simple low capacity pump or, if used in a hospital, the source may be the usual compressed air or oxygen supply. In either case the available pressure may be from about 8 to 20 pounds per square inch gauge pressure, depending upon the results desired.

As air enters the tube 9 it passes to plenum 13 and is discharged through aperture 15. Air also travels down pump air tube 17 where it is throttled to a lower pressure either by the internal diameter of the tube or a suitable throttling valve (see FIG. 4), and exhausts from the terminal upward leg 19 thereof into lift tube 28 thus forming a bubble pump to lift liquid from the base flask 10 through tube 28 so as to be discharged through outlet 31 into holding receptacle 25. The air bubbles issuing from outlet 31 escape through annulus area 41. Because of the position of the upper end 37 of tube 29 there is an accumulation of the liquid until the level thereof reaches the upper end of and overflows down the tube 29. This arrangement eliminates pulsations from the liquid in the reservoir 25 such as are created by the discharge of the bubble pump thereinto, so that the flow through tube 29 is even and regular. The liquid discharges onto the surface of plenum chamber 13 and films out to flow completely over top of the spherical surface where in a highly stressed condition it is ruptured by the issue of air or gas from aperture 15 and a portion of the liquid is dispersed upwardly in a fine mist of spheroid-like particles in the phenomenon explained in the identified Babington et al. patents.

While the spray is more uniform than that produced in other nebulizers there are some particles which are of non-uniform size being larger than the majority of particles generated at chimney end 27. Since they are larger and because of the very low air flow through aperture 15, the large particles are not carried along in the airstream as far as the smaller particles. Thus, gravity will affect the larger particles and cause same to traverse a divergent path or "fan out" while the smaller particles travel vertically up through chimney 26. The tendency of the larger particles to fan out causes same to impinge upon the inner surface of chimney 26 where the larger particles collect in drops and fall back into the base chamber 10 along with the non-atomized portion of the liquid film flowing over plenum chamber 13. Thus, the atomized or nebulized emission of liquid from chimney 26 is characterized by the uniform and small size of the particles.

It has also been found that the shape of chimney 26, i.e., the relatively narrow throat and the flaring bottom 27 produce a definite ejector action which has a significant benefit on the flow of the smaller uniform particles and little, if any, effect on the larger particles since most of these latter have coagulated on the walls of chimney 26 before the full ejector effect takes place.

It has also been found that the emission of uniform particles from chimney 26 is enhanced by the provision of aspirating apertures 5 in the base receptacle 10 in the vicinity of plenum 13, but below the edge of closure assembly 20. Thus, the aspirating air drawn in through apertures 5 rushes into the low pressure region created by the air or gas discharging through aperture 15 with the result that the total air flow up chimney 26 is much greater than that which is required to nebulize the liquid. This in turn increases the velocity in chimney 26 so as to carry the particles upward in a mixture of aspirated and atomizing air, yet not sufficient to affect the tendency of the larger particles to fan out from the stream flowing up through chimney 26.

MODIFICATIONS OF BASIC UNIT

As shown and described thus far, the nebulizer unit has utility as a simple home-use vaporizer. If intended for such use, the base flask is simply filled with water and, perhaps, a typical inhalent-type of medicant. A pump unit, such as a conventional low capacity, electrically-driven type will be supplied for attachment to air conduit 9. The very same unit can also be used in more sophisticated applications. For example, a tube or flexible hose may be slipped over the end of chimney 26 and the output from the unit directed into a croup tent or the like or in some instances to a face mask. The very same unit can also be used in hospitals without modifications. All of the defined uses, room vaporizer, croup tent, etc., are accomplished in precisely the same manner except that since most hospitals have built-in compressed air and/or oxygen outlets in each room, the pump may be disconnected and the tube 9 connected directly to such supply.

It has been found by tests that a basic unit of the type described herein requires about 5–10 liters per minute of atomizing air at 15 p.s.i.g. to vaporize 25 cubic centimeters of liquid per minute into a mist with a mass median diameter of less than 7 microns. This output compares favorably with all known vaporizers in use today and is adequate for almost any general medical application in which vaporizers are required.

There are also uses for medical nebulizers where it is necessary to vary capacity and where versatility such as feed regulation, continuous operation, etc., are most desirable. All of these requirements may be accomplished by the same basic unit shown in FIG. 1 with but very slight modifications. By simply changing the size of orifice 15 a corresponding increase in capacity can be obtained. In fact, in practice it may be that one unit could be marketed to include all of the features to be described, which unit would meet every practical known use for vaporizers and nebulizers. Expense would dictate this aspect however, since it is desirable to provide such units to the general public at a price which would be within the reach of anyone in need of such equipment such as children with cystic fibrosis, asthmatic or emphysema sufferers and the like, who are in dire need of reasonably-priced nebulizing apparatus for home use.

In any event utility of the basic device is expanded considerably by incorporation therein of the modifications illustrated in FIGS. 2 through 9.

Turning first to FIGS. 2 and 3, the modification disclosed enables use of the apparatus with an external supply such as pre-mixed inhalents supplied in separate sterilized containers 100 which may be suspended from a hook 101 for gravity feed to a nebulizer in accordance with present medical practices. As shown the container 100 is provided with two hoses 103 and 105 which are inserted through a conventional connection to the contents therein. One of the hoses 103 is connected to a simple elbow tubular fitting 107 having one branch extending through wall 7' of base flask 10'. As shown the elbow is inserted through the wall 7' and held in place therethrough by means of a conventional grommet 110, though same could just as well be formed integrally with wall 7 or welded or soldered or otherwise fixed therein. As shown in FIG. 2 the vertical branch of elbow conduit 107 extends down into base flask 10' some distance below the normal liquid level maintained in flask 10' as may be indicated by the fill mark 50'. The other connector to medicant bottle 100, namely tubular conduit 105 is connected to a second elbow 111 which also is mounted through wall 7' of base flask 10' via a conventional grommet 110'. The wall penetrating branch of elbow 111 is connected by flexible tubing 105 to the medicant bottle 100 via a standpipe 112 which extends up toward the bottom of the inverted bottle. The vertical branch of elbow 111 terminates at a point substantially in horizontal alignment with the fill mark 50'.

Thus, base flask 10' is initially filled with the medicant to be nebulized, the connections made between bottle 100 and flask 10' via flexible conduits or tubes 103, 105 and the nebulization is started as described above. As the level of medicant drops in flask 10' the lower end of elbow 111 is exposed to atmospheric air. Thus, air is admitted to medicant bottle 100 and the medicant flows down flexible conduit 103 to replenish the liquid in flask 10' until the liquid level again seals off the bottom end of elbow 111. For proper operation, and so that the atmospheric air bubble entering the vertical leg of elbow 111 can travel upward to medicant bottle 100, conduit 105 should have a continuous slope. The brief afterflow of medicant creates a vacuum in bottle 100 thus, stopping the feed of medicant to flask 10' until the liquid level again falls and the whole process is repeated automatically. Obviously, then depending on the capacity of bottle 100 the nebulizer can be operated continuously without attendance until the entire medicant content of bottle 100 is exhausted. It might also be noted that the flask 10' of FIG. 2 shows but another base flask configuration of which there are limitless variations.

Proceeding further, to FIG. 4 a further modification is disclosed in the form of a modified plenum and air pump tube. Again, this assembly is removably mounted via a grommet 120 through the side wall 7 of base flask 10. The plenum chamber 13' is a hollow sphere from which extends conduit 9' through the grommet 120. Branch tube 17' is in communication with air conduit 9' but in this instance a simple bypass throttle valve is provided whereby the amount of air bled through pump air tube 17' can be controlled. For simplicity's sake the valve is illustrated as a simple needle valve having a needle 122 having a conical point 124 which seats against seat 126. A finger manipulator 128 permits needle 122 to be turned whereby the action of threads 130 thereon cooperating with threads 132 in base 134 serve to raise and lower point 124 from or toward seat 126. It will be appreciated that almost any type of valve can be used to permit regulation of the air flow to pump air line 17'. While regulation of the air to pump the liquid from base flask 10 to the holding reservoir 25 is not always necessary, there are times when it may be desirable to do so, so that the volume of fluid pumped is relatively constant despite variations in air pressure to plenum 13.

An additional and advantageous modification of the nebulizer is also shown in FIG. 5. In this structure the base flask 10 is provided with an immersion heater 130 extending through wall 7 closely adjacent the bottom 1 thereof. Heater 130 may be mounted in any manner in wall 7 being shown mounted via a typical liquid sealing grommet 125. It is of a standard type 110–120 volt resistance heater which may use the ordinary house current power and has a capacity to raise the contents of the flask 10 to about 120° F.

In respect of this latter modification it has been found that by the simple addition of heat to the water, the output of the basic unit in cubic centimeters of medicant nebulized can be improved by at least 50 percent all other factors being equal. At 120° F. the liquid is not so hot as to constitute a burn or scald danger if the unit were accidentally spilled and, even more interesting, the temperature of the vapor-air mixture leaving the unit (because of evaporative cooling) is approximately 80° F. which in certain applications may be extremely desirable since the medicant is inhaled at close to body temperature by the patient.

HIGH PERFORMANCE MODIFICATION I

A further modification of the nebulizer is shown in FIG. 6. This structure incorporates all of the essential elements defined in the first described unit. The particular advantages of this latter unit are compact design and increased output and density in terms of medicant output per liter of carrier air or other gas.

As shown, the unit includes a medicant liquid holding base receptacle 101. The base receptacle 101 is provided with a discharge nozzle 147 formed integrally therewith. Spaced some distance back from the end of nozzle 147 at an area 130 where the nozzle necks down is provided a series of apertures 131 which are induction parts operating in the same fashion as ports 5 of the FIG. 1 device. Again the base receptacle is provided with an aperture in which is mounted an air inlet tube 109 which terminates in a spherical plenum chamber 113 having an aperture 115 formed in its end diametrically opposite tube 109. Air inlet tube 109 is provided with two branches, one brancg forming the pressure conduit 128 for bubble pump assembly 120. The second branch 114 also terminates in a spherical plenum chamber 113' having an aperture 115' therein, the aperture 115' being alined horizontally with aperture 115.

Disposed directly above the two spherical plenum chambers 115 and 115' is a holding reservoir 125 having two downwardly directed discharge conduits 129, 129' each of which is aligned vertically above the plenum chambers 115 and 115' respectively. A protrusion or dam 127 is interposed in the liquid inlet to the reservoir to establish a liquid level above the lower surface of the reservoir.

The holding reservoir 125 is in communication with the feed conduit 128' having a flared terminal end 133' disposed directly above the end of pressure conduit 128 which completes bubble pump assembly 120.

OPERATION OF HIGH PERFORMANCE UNIT I

The operation of this device is precisely as stated with respect to the apparatus of FIG. 1 configuration. Liquid in base receptacle 101 is pumped via bubble pump assembly 120 to holding reservoir 125 and is discharged therefrom onto the spherical surfaces of plenum chambers 113 and 113'. Air which is entrained in the lifted liquid is vented from reservoir 125 through vent hole 126. Thus, holding reservoir 125 acts as an accumulator chamber to assure even flow of liquid to the surfaces of the spherical plenum chambers 113 and 113'. The protrusion or dam 127 in the entrance to the holding reservoir 125 acts to eliminate turbulence and fluctuations in the liquid level, and insures an even flow of liquid over both plenum chambers.

It should also be understood that the modifications shown in FIGS. 2, 3 and 4 can also be adapted to the configuration shown in FIG. 6. In particular the external feed system to reservoir 101 is particularly adaptable to the FIG. 6 form of nebulizer.

A unit similar to that shown in FIG. 6, as will be discussed, has shown itself to be capable of superior performance, an experimental unit having delivered approximately 20,000,000 liquid particles per cubic centimeter of carrier air. In the model tested the front sphere 113' was provided with a single discharge slot 115' while the rear sphere 113 was provided with a pair of slots or apertures 115, same being positioned in a common horizontal plane passing through the center of the sphere as illustrated in FIG. 6a. Preferably, the included angle a between the openings 115'' and 115''' is on the order of 75°.

By way of explanation of the superior performance of this configuration of nebulizer, it is believed that with the use of a series of atomizing chambers, the mist from the rear atomizer is entrained into that produced by the front atomizer. In this manner, the spray from the rear atomizer more effectively and efficiently fills the voids between the liquid particles produced by the front atomizer. By contrast, when multiple sprays emit from a single atomizer, more turbulence occurs and the collision rate is greater. Both of these factors cause agglomeration of particles and subsequent "rain-out" or deposition of particles within the nebulizer or distribution hose. For example, in a single atomizer design utilizing multiple slots, it is highly probable that a large nonrespirable particle (i.e., greater than 10 microns) will collide with a highly respirable particle of 2 or 3 microns, and prevent the smaller particle from negotiating the distribution hose and being inhaled by the patient. On the other hand, if the two droplets were produced in a series configuration, with the front atomizer producing the larger particle and the rear atomizer producing the smaller particle, it is highly probable that the small particle would be sucked into one of the void spaces in the mist produced by the front atomizer. In so doing, it would be carried along through the distribution hose and add to the mist density produced by the total nebulizer configuration. By locating atomizers in series, the larger or non-respirable particles produced by the second or third atomizers in the series, never reach the spray plume of the forward atomizer, because their decaying trajectory causes them to rain-out. This serves to keep the nebulizer from becoming cluttered with non-respirable large particles, which in turn reduces the possibility of collision and agglomeration. In addition, by locating atomizers in series, the relative velocity of the spray particles produced by the individual atomizers is reduced. This promotes more efficient droplet entrainment which in turn allows more liquid particles to be transported per volume of carrier air.

HIGH PERFORMANCE UNIT II

Turning now to FIG. 7, a further modification designed to enhance the aerosol producing ability of the basic nebulizer is shown. In FIG. 7 only the nebulizing section is shown, it being understood that air and the liquid, medicant or water or a combination of both, may be introduced into the apparatus by any of the means previously described. The nebulizer section includes a hollow chamber 150 having a closed end 151 and an opening 152. The chamber is generally elongated along a horizontal axis A—A passing through its center.

Disposed within chamber 150 concentric with axis A—A is an elongated cylindrical tubular shroud 153 having one end 154 spaced from closed end 151 of the chamber and the other end 155 spaced well within the chamber 152 and away from opening 152. Also disposed within the chamber 150 and the cylindrical member 153 and centered on axis A—A is a hollow sphere 156 having openings 157, 157' diametrically opposed and aligned on a diameter corresponding to axis A—A. The opening 157' is smaller than opening 157 for purposes to be described.

Positioned directly above the hollow sphere is downwardly directed liquid admitting tube 158 having its end spaced slightly above sphere 156 and being in further communication at its other or upward end with a settling or holding reservoir 159 which is in turn provided with a liquid inlet 160.

A plurality of apertures 161 are provided in chamber 150 at a point slightly behind the leading or right-hand edge (as shown in FIG. 7) of the member 155. These apertures, as will be noted subsequently, are what may be called aspirating ports.

OPERATION OF HIGH PERFORMANCE UNIT II

Liquid is introduced at 160 into the settling chamber 159 where any pulsations entrained, air, etc., settle out before it passes down tube 158 and is deposited on the outer surface of the hollow sphere 156. As set forth the rate of flow is such that the surface of the sphere over the apertures 157, 157' is covered by a continuous dynamic film. The liquid in excess of that which is atomized or aerosolized is discharged from the bottom area of the sphere and collected by any suitable means (not shown) and recirculated back into the liquid supply system.

Relatively low pressure air, in the range mentioned in connection with the basic nebulizer, is introduced into the sphere and discharges from the small outlets 157, 157'. At the same time, the liquid, be it simply water or a water-medicant combination of any desired ratio, is caused to fill the holding reservoir 159 and begins to discharge from outlet 158 to flood the surface of the sphere, flowing over the openings 157, 157'. Due to the differential in output created by the relatively larger size of opening 157 the aerosolized liquid is discharged outwardly of the chamber via mouth 152. This flow creates an area of reduced pressure at the closed end such that aspirating air is caused to enter openings 161 and flow rearwardly toward the end 151 between the chamber wall and the internal cylindrical shroud 153. As the aspirated air passes beyond the rear end 154 of the shroud 153 its path of flow is reversed and it travels toward the sphere 156 where it encounters aerosolized liquid created by the air flow through the smaller opening 157'. Thus the aspirated air is moisture conditioned as it travels through cylindrical shroud 153 in the direction of end 155 thereof and encounters the aerosolized medicant or whatever that is created by the opening 157.

Thus, in effect, the air is preconditioned as close to the point of saturation as is possible before it emerges from the shroud with the result that the aerosolized liquid created at opening 157 remains in suspension in virtually its entirety since none of its is evaporated simply to raise the relative humidity of the air traveling through the interior of the shroud.

MODIFICATIONS OF FIGS. 8, 9 and 10

In FIGS. 8, 9 and 10 there are disclosed additional modifications of the basic concept whereby the mass median diameter of aerosolized liquid produced by the basic device of FIGS. 1, 6 or the modification of FIG. 7 may be markedly increased. All of these modifications utilize the principle that it is possible to impact air entrained liquid particles to physically break up the particles to smaller size.

Thus in FIG. 8, there is disclosed the use of two spheres 180, 182, each having a single aperture 184, 186 respectively and means 188, 190 for discharging a liquid film onto the spheres for atomization according to the principles described previously. The outlets 184, 186 are so positioned that the air emerges therefrom on a collision or intersecting path. Preferably, the included angle formed by coplanar intersecting lines passing through the openings 184, 186 would be 90° or less.

A variation of this arrangement is also disclosed in FIG. 10 where the spheres 180', 182' are positioned with the openings 184', 186' in mutually opposed relationship or, expressed in terms of included angle, this angle is 180°.

In both of the above noted arrangements, the air emerges from the openings 184, 186, 184', 186' to cause the liquid being filmed over the respective spheres to be aerosolized in part. The particles of aerosolized liquid from one sphere are impacted against the particles dispersed from the other sphere to further reduce the particle size. While reduction in particle size is obtained in the FIG. 10 arrangement, this configuration represents an extreme because:

a. The opposed air flows have a disruptive effect on the liquid films flowing over the surfaces of the respective spheres, b. The air streams tend to neutralize each other hence some additional means must be used to cause movement of the aerosolized medicant or liquid from the impact area.

In general then, the advantages of impaction are somewhat complicated by the additional factors introduced into a system in the FIG. 10 configuration. However, as the relationship of the openings is varied more and more toward the FIG. 10 configuration from the FIG. 8 configuration, the aerosol density is increased because the neutralized air streams cannot provide conditions whereby the air streams aspirate additional air. However, as the FIG. 8 configuration is approached, the aspirated air increases as the included angle between the opposing air streams decreases.

Considering, further, the results obtained by impacting, reference is now made to FIG. 9, which discloses a highly effective means for obtaining the results desired. In this modification the usual sphere with its very small opening is combined with a stationary impactor. As shown, the impactor is a stationary ball or sphere 190, positioned so as to lie directly in the path of air emitted from the opening 192. Thus the liquid introduced onto the surface of the sphere is aerosolized by the emitter air and immediately is impacted against the impactor ball 190 to further reduce the size of the aerosolized particles.

The use of various types of impactors to shatter droplets is not a new technique in the field of liquid atomization and nebulization. However, in the case of the new atomization concept herein involved the impaction stage is more efficient. This can be attributed to the fact that the impactor can be located close to the discharge orifice where the kinetic energy of the droplets, and hence the shattering efficiency, is high. This is attributable, in the subject invention, to the fact that the droplets are formed from the thin film without passing through the usual ligament phase found in conventional pneumatic systems. By way of comparison, an impactor on a conventional atomizer cannot be located close to the discharge orifice because of the presence of a ligament phase of atomization which always precedes the final formation of droplets. When properly placed in the droplet regime of the spray plume, the impactor on a conventional atomizer is relatively far from the discharge orifice, and at a point where the liquid particles have begun to diverge and lose momentum. As a result many of the particles strike only a glancing blow against the impactor, and the impingement velocity is reduced. This in turn reduces the overall effectiveness of the droplet shattering process in the case of the conventional system.

Soon after the use of impactors was initiated, it was found that an aerosol could be produced that was equal to or better than that produced by any known atomizing concept or device. In the initial impactor experiments, it was found that the capacity and density of a model of nebulizer generally conforming to the FIG. 1 configuration could be increased approximately 50 percent by the addition of a spherical impactor located in front of the discharge orifice. Tests conducted on a counterflow-single atomizer design as shown in FIG. 7 provided results comparable to the results obtainable by the best available ultrasonic nebulizer. Application of the impactor technique to the modification disclosed in FIGS. 6 and 6a produced the highest quality aerosol of all the prototype units. Recent data has revealed that the unit delivers approximately 20,000,000 liquid particles per cubic centimeter of carrier air. This is at least twice as many as that produced by any known technique for producing aerosolized liquid for therapeutic purposes.

From the above description it is believed apparent that various modifications and configurations of atomizer devices may be combined to produce nebulizer devices capable of performing tasks ranging from simple room humidification to sophisticated inhalation therapy such as required in hospitals. All of the various changes in configurations and combinations are readily manufactured and embrace the fundamental goals of the invention, to wit, simplicity of design, ease of cleaning, uncomplicated use and relative inexpensiveness as compared with known products.

Having thus described the invention, it is apparent that combinations and modifications all falling within the skill of the art will occur to others and that such combinations and modifications fall within the spirit and scope of the claimed subject matter, wherein:

What is claimed is:

1. A nebulizing unit comprising in combination, a base flask having an open top; a closure member for said flask, said closure member including at least one vertical chimney having a flaring lower end; a collar surrounding the lower end of the chimney and defining first, a support for the chimney and, secondly, with the chimney end, an annular holding reservoir; a first conduit opening into said reservoir and having a lower terminal end disposed beneath the reservoir at a point closely adjacent the bottom of the base flask; at least a second conduit opening into said holding reservoir and having one end disposed in the lowermost point thereof and the opposite end disposed below the bottom of the holding reservoir and projecting into the base flask adjacent its mouth; at least one plenum chamber having a spherical end with an aperture therein disposed within the base flask and beneath the terinal end of said second mentioned conduit; and its opposite end disposed outside of the side wall of said base flask; a branch line in communication with said plenum chamber and having a terminal end disposed adjacent the bottom of said base flask and in registry with said first mentioned conduit opening into said holding reservoir and discharging therein.

2. The combination defined in claim 1, wherein the base flask is provided with apertures through its side wall, said apertures being positioned in a plane slightly above the plane of said plenum chamber.

3. The combination defined in claim 1 including a dome-shaped cap having a central opening telescoped over said chimney and having its peripheral edge-seated on said collar.

4. The combination defined in claim 1 wherein said flask, said collar and chimney assembly and said plenum chamber are integral units removably assembled to form a nebulizing unit.

5. A nebulizer as defined in claim 1 including further heating means disposed in said base flask closely adjacent the bottom thereof.

6. A nebulizer as defined in claim 1 including, further, an adjustable valve means at the point of communication with said branch line for regulation of flow through said branch line.

7. A nebulizer defined in claim 1 including further a pair of tubular, elbow shaped connector transcending the side wall of the base flask and disposed with their vertical branches just beneath the lower portion of said spherical plenum chamber, one conduit terminating at a point spaced above the terminal end of the vertical branch of the other conduit.

8. A nebulizer as defined in claim 1 wherein all of said parts are fabricated of a non-corrosive, non-rusting, non-permeable material having the characteristic of resistance to high temperature.

9. A nebulizer as defined in claim 1 wherein said material is glass.

10. A nebulizer as defined in claim 1 wherein said material is metal.

11. A nebulizer as defined in claim 1 wherein said matrerial is a plastic.

12. A nebulizing device comprising a base receptacle; a [pump] *pumping means* in said base receptacle for raising liquid from said receptacle; said [pump] *pumping means* having an outlet; a reservoir above *the liquid level in* said base receptacle and in communication with the [pump] outlet *of said pump means* to receive the output of said [pump] *pumping means* and having *first* outlet means; at least one [spherical] *hollow* plenum chamber having an aperture therein being disposed adjacent the *said first* output let means from said reservoir, said [spherical] plenum *chamber* receiving the output from said *first* outlet means on its outer surface, *said plenum chamber having a smooth convex curved surface over at least the portion thereof over which flows the liquid from its impingement on said outer surface towards and past said aperture,* whereby *said* liquid discharged [thereon] *onto said outer surface* will spread out in a thin, stressed film before passing over the aperture in said plenum *chamber*; a source of gas under pressure communicating with the interior of said [spherical] plenum *chamber*, said gas issuing from the aperture therein, and [an] *a second* outlet means [from] *for* said base receptacle positioned in the direction of the gas exiting through said aperture, said *second* outlet means being sized [and ported] to define [and] *an* ejector [to draw], *and porting means for drawing* ambient air [through] *into* said [outlet] *receptacle* to comingle same with the nebulized liquid exiting from said *second* outlet.

13. The combination defined in claim 12, including heater means for heating the liquid in said base receptacle.

14. The combination defined in claim 12 including a liquid supply source for automatically replenishing the liquid in said base [flask] *receptacle.*

15. The combination defined in claim 12 including a pair of plenum chambers having apertures discharging toward said *second* outlet means.

16. The combination defined in claim 15 including plural *first* outlet means for said reservoir.

17. A nebulizer comprising at least one [spherical] *hollow* plenum chamber having an opening therein, *said plenum chamber having a smooth convex curved outer surface over at least a portion thereof,* means to flood the *outer* surface of the [sphere] *plenum* with liquid to be nebulized, means [to introduce] *for producing a fine mist of spheroid-like particles of the liquid flowing over said outer surface without a transitional ligament phase by introducing* air above ambient pressure into the interior of the [sphere] *plenum* for discharge through said opening, impactor means positioned in the path of said air discharge whereby particles of the nebulized liquid are further reduced in size by contact with said impactor, *said impactor being positioned at a distance sufficiently close to said opening of said plenum as to ensure impingement of liquid droplets with high kinetic energy upon the outer surface of said impactor, said distance being such that, if used in a conventional atomizer, the liquid would impinge upon the impactor while still in the ligament phase.*

18. A nebulizer as defined in claim 17 wherein said impactor means comprises a second [spherical] *hollow* plenum chamber having *a smooth convex curved outer surface over at least a portion thereof and* an opening therein discharging so as to cause impact between the particles of nebulized liquid in the opposed air stream from said first [spherical] plenum chamber.

19. A nebulizer as defined in claim 17 wherein said [spherical] plenum chamber is provided with a pair of openings lying in a common plane passing through the center of the [spherical] chamber and wherein the spacing between the openings is defined by an angle $\alpha$.

20. A nebulizer as defined in claim 18 wherein $\alpha$ is 75°.

21. A nebulizer as defined in claim 12 wherein a second [spherical] plenum chamber is disposed in alignment with the behind said first mentioned [spherical]

chamber and said second plenum chamber is provided with multiple openings.

22. A nebulizer comprising a source of liquid to be nebulized and an outlet for said nebulized liquid comprising a hollow [spherical] plenum chamber axially aligned with said outlet *having a smooth convex curved outer surface over at least a portion thereof* and [having] apertures therein, one of said apertures facing said outlet, the other of said apertures being diametrically opposed to discharge in the opposite direction, a hollow tubular conduit aligned with said outlet and surrounding said [sphere] *plenum chamber* a closed chamber surrounding but spaced from said tubular conduit, said chamber having air passages therein adjacent to but behind the outlet end of said tubular conduit, means for introducing liquid from said source to the outer surface of said [spherical] plenum chamber and means for introducing air above ambient pressure into the interior of said plenum chamber.

23. A nebulizer as defined in claim 22 wherein all of said parts are fabricated of a non-corrosive, non-rusting, non-permeable material having the characteristic of resistance to high temperature.

24. A nebulizer as defined in claim 22 wherein said material is glass.

25. A nebulizer as defined in claim 22 wherein said material is metal.

26. A nebulizer as defined in claim 22 wherein said material is a plastic.

* * * * *